(12) United States Patent
Sako et al.

(10) Patent No.: US 10,315,827 B2
(45) Date of Patent: Jun. 11, 2019

(54) BIOIMPLANT PACKAGE AND BIOIMPLANT PACKAGING METHOD

(71) Applicant: KYOCERA Corporation, Kyoto-shi, Kyoto (JP)

(72) Inventors: Tatsuya Sako, Kyoto (JP); Tomoyuki Nakaji, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/578,431

(22) PCT Filed: Jun. 7, 2016

(86) PCT No.: PCT/JP2016/066879
§ 371 (c)(1),
(2) Date: Nov. 30, 2017

(87) PCT Pub. No.: WO2017/002549
PCT Pub. Date: Jan. 5, 2017

(65) Prior Publication Data
US 2018/0170648 A1    Jun. 21, 2018

(30) Foreign Application Priority Data

Jun. 29, 2015 (JP) ................................ 2015-130110

(51) Int. Cl.
*B65D 81/20* (2006.01)
*B65D 81/05* (2006.01)
(Continued)

(52) U.S. Cl.
CPC ............ *B65D 81/05* (2013.01); *A61F 2/0095* (2013.01); *B65D 5/029* (2013.01); *B65D 5/0281* (2013.01);
(Continued)

(58) Field of Classification Search
CPC .. B65D 81/025; B65D 81/2023; B65D 81/02; B65D 77/02; B65D 5/0281; B65D 5/029;
(Continued)

(56) References Cited

U.S. PATENT DOCUMENTS 4,611,456 A * 9/1986 Gillio-tos ............. B65D 75/305
156/287
6,161,695 A * 12/2000 Nicolais ................ A61F 2/0095
206/438
(Continued)

FOREIGN PATENT DOCUMENTS

JP        3078992 U     10/2012

*Primary Examiner* — Luan K Bui
(74) *Attorney, Agent, or Firm* — Volpe and Koenig, P.C.

(57) ABSTRACT

A bioimplant package according to an embodiment of the present invention includes a sealing body to vacuum seal a bioimplant therein, and an inner box to accommodate the sealing body therein. The sealing body vacuum seals the bioimplant so that the bioimplant is located at a middle part of the sealing body. The inner box is made of an approximately rectangular-shaped sheet material divided into a mounting part to mount thereon the middle part of the sealing body, and a pair of winding parts which windingly fix a side part of the sealing body extending outward from the mounting part and come into linear contact with the sealing body in the vicinity of a boundary part with the mounting part. A bioimplant packaging method according to an embodiment of the present invention is a method for packaging a bioimplant by using a bioimplant package according to the above embodiment.

16 Claims, 6 Drawing Sheets

(51) Int. Cl.
| | |
|---|---|
| *B65D 5/50* | (2006.01) |
| *A61F 2/00* | (2006.01) |
| *B65D 77/02* | (2006.01) |
| *B65D 5/02* | (2006.01) |
| *B65D 5/04* | (2006.01) |
| *B65B 5/04* | (2006.01) |
| *B65D 81/02* | (2006.01) |
| *A61F 2/36* | (2006.01) |

(52) U.S. Cl.
CPC ............... *B65D 5/04* (2013.01); *B65D 5/50* (2013.01); *B65D 77/02* (2013.01); *A61F 2/36* (2013.01); *B65B 5/045* (2013.01); *B65D 81/025* (2013.01)

(58) Field of Classification Search
CPC .. B65D 5/04; B65D 5/50; B65B 5/045; A61F 2/36; A61F 2/0095
USPC ......... 206/438, 449, 524.8, 525, 525.1, 583, 206/784, 829; 53/403
See application file for complete search history.

(56) References Cited

U.S. PATENT DOCUMENTS

| | | | | |
|---|---|---|---|---|
| 6,675,973 | B1* | 1/2004 | McDonald | B65D 5/5028 206/521 |
| 6,889,839 | B1* | 5/2005 | Rosten | B65D 81/075 206/363 |
| 2005/0092636 | A1* | 5/2005 | Su-Syin | A61L 2/07 206/363 |
| 2008/0223750 | A1* | 9/2008 | McDonald | B65D 5/5028 206/583 |
| 2011/0240515 | A1* | 10/2011 | Ridgeway | B65D 5/5028 206/583 |
| 2015/0239635 | A1* | 8/2015 | McDonald | B65D 81/075 206/583 |

* cited by examiner

BIOIMPLANT PACKAGE AND BIOIMPLANT PACKAGING METHOD

TECHNICAL FIELD

The present invention relates to a bioimplant package and a bioimplant packaging method.

BACKGROUND ART

The present applicant previously developed a bioimplant package as described in Patent Document 1. The package is capable of stably packaging, for example, an artificial hip joint stem that is one of bioimplants. The package preferably has a simpler configuration.

PRIOR ART DOCUMENT

Patent Document

Patent Document 1: Japanese Utility Model Registration No. 3178992

SUMMARY

Problems to be Solved by the Invention

One of the problems to be solved by the present invention is to provide a bioimplant package and a bioimplant packaging method, with which the bioimplant is stably packageable with a simple configuration.

Means for Solving the Problems

In an embodiment of the present invention, a bioimplant package includes a sealing body which is composed of a gas impermeable film material and configured to vacuum seal a bioimplant therein, and an inner box configured to accommodate the sealing body therein. The sealing body is configured to vacuum seal the bioimplant so that the bioimplant is located at a middle part of the sealing body. The inner box is made of an approximately rectangular-shaped sheet material divided into a mounting part configured to mount thereon the middle part of the sealing body, and a pair of winding parts configured to windingly fix a side part of the sealing body extending outward from the mounting part and configured to come into linear contact with the sealing body in the vicinity of a boundary part with the mounting part. The mounting part and the pair of winding parts are located sequentially in a direction from a middle part toward each of a pair of opposing side edge parts in the inner box.

In an embodiment of the present invention, a bioimplant packaging method is a method for packaging a bioimplant by using the bioimplant package according to the above embodiment. The method includes: vacuum sealing the bioimplant by the sealing body so that the bioimplant is located at the middle part of the sealing body; and accommodating the sealing body into the inner box in a state in which the side parts of the sealing body extending outward from the mounting part are windingly fixed and also brought into linear contact with the sealing body in the vicinity of the boundary part with the mounting part, by winding each of the pair of winding parts after mounting the middle part of the sealing body on the mounting part of the inner box.

Effects of the Invention

The bioimplant package and the bioimplant packaging method according to the embodiment of the present invention produce the effect that the bioimplant is stably packageable with the simple configuration.

BRIEF DESCRIPTION OF THE DRAWINGS

FIG. 2 is a diagram showing the bioimplant package shown in FIG. 1.

FIG. 3 is a diagram showing a sealing body included in the bioimplant package shown in FIG. 1.

FIG. 4 is a diagram showing an inner box included in the bioimplant package shown in FIG. 1.

FIG. 5 is a diagram showing an outer box included in the bioimplant package shown in FIG. 1, FIG. 6 is a diagram showing an outer box included in a bioimplant package of a comparative example.

EMBODIMENTS

<Bioimplant Package>

Figure 1A:
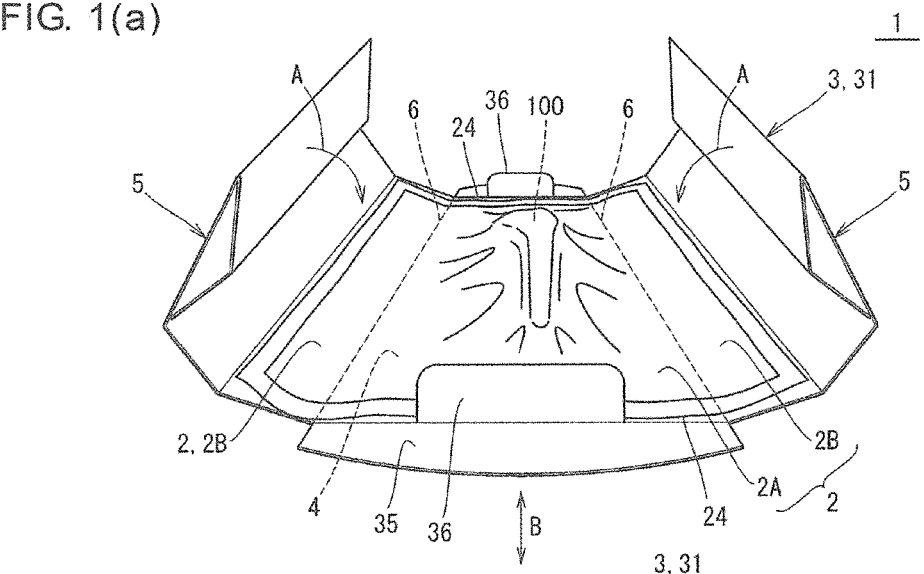
FIGS. 1(a) to 1(c) are schematic explanatory drawings showing a bioimplant package according to an embodiment of the present invention.

The bioimplant package (hereinafter also referred to as "package") according to an embodiment of the present invention is described in detail below by taking, for example, the case where the bioimplant is an artificial hip joint stem (hereinafter also referred to as "stem") with reference to FIGS. 1 to 5.

As shown in FIG. 1, the package 1 of the present embodiment is the package for the stem 100. The stem 100 is a femoral component of the artificial hip joint, which is composed of a Ti alloy or the like, and is an approximately bar-shaped curved member. The package 1 of the present embodiment intended to package the stem 100 includes a sealing body 2 for vacuum sealing the stem 100, and an inner box 3 for accommodating the sealing body 2 therein.

(Sealing Body)

The sealing body 2 is a flexible hollow member for vacuum sealing the stem 100 therein as shown in FIG. 3. The term "vacuum sealing" denotes sealing in a state in which an internal air pressure is controlled at an air pressure lower than at least atmospheric pressure.

The sealing body 2 is made of a gas impermeable film material 22. In terms of gas impermeability of the film material 22, a water vapor transmission rate measured according to JIS Z0222 is preferably 0.5 g/(m²·d) or less. The film material 22 preferably retains the gas impermeability over a long term. Specifically, when a sterilization expiration period is five years, the film material 22 preferably retains the gas impermeability over five years or more.

For the purpose of improving the gas impermeability of the film material 22, at least one of a gas impermeable thin film and a vapor deposited film composed of an inorganic oxide is preferably laminated on a surface of the film material 22. The gas impermeable thin film can be deposited by, for example, applying a coating solution containing alkoxide and water-soluble polymer to the surface of the film material 22, followed by drying by heating. Examples of the inorganic oxide in the vapor deposited film include amorphous silicon oxide and aluminum oxide each having transparency. Examples of the method of depositing the vapor deposited film include vacuum vapor deposition method, sputtering method, ion plating method, and ion cluster beam method.

The film material 22 preferably has, besides gas impermeability, the following physical properties. That is, the film 22 is preferably capable of being subjected to sterilization treatment for medical devices, such as gamma irradiation sterilization. The film material 22 preferably also has thermosetting property. This makes it possible to carry out heat sealing, and it is therefore easy to carry out a sealing operation described later. The film material 22 preferably has bacterial impermeability. Thus, sterility of the stem 100 after subjected to the sterilization treatment is retainable over a long term. The film material 22 preferably has transparency. Thus, the stem 100 after subjected to the vacuum sealing is visually observable from the outside of the sealing body 2.

The film material 22 is composed of, for example, a synthetic resin. Examples of the synthetic resin include polyolefin-based resins, such as polyethylene and polypropylene; polyester-based resins, such as polyethylene terephthalate, polyethylene isophthalate, polyethylene-2,6-naphthalate, and polybutylene terephthalate; vinyl-based resins, such as polyvinyl alcohol, ethylene-vinyl acetate copolymer saponification product, and soft polyvinyl chloride; silicone-based resins; and polyamide-based resins. These synthetic resins may be used alone or jointly with two or more kinds.

The sealing body 2 of the present embodiment composed of the film material 22 described above is made of a laminated body 21 in which peripheral edge parts 221 and 221 of a pair of film materials 22 and 22 are overlapped with each other and sealed together. With this configuration, it is easy to vacuum seal the stem 100 as follows.

Figure 3A:
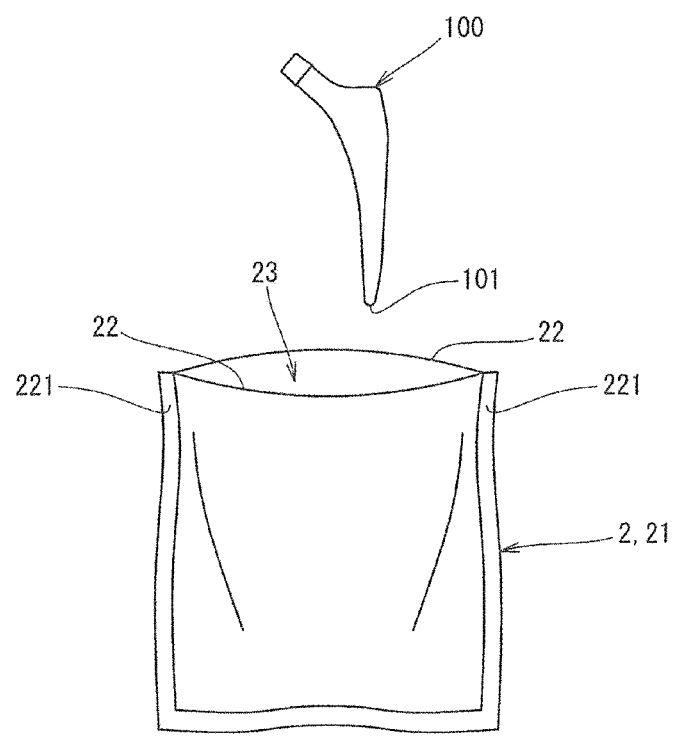
FIG. 3(a) is a schematic explanatory diagram showing a state before vacuum sealing the bioimplant.
Figure 3B:
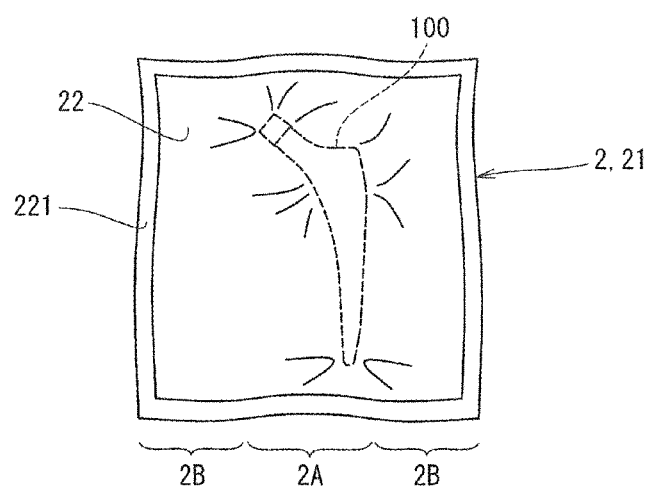
FIG. 3(b) is a schematic explanatory diagram showing a state after vacuum sealing the bioimplant.

Specifically, as shown in FIG. 3(a), when the peripheral edge parts 221 and 221 are overlapped with each other and sealed together, a part thereof is left in a non-sealed state so as to make a bag shape having an opening 23. Subsequently, the stem 100 is stored through the opening 23 into the laminated body 21. Finally, as shown in FIG. 3(b), the vacuum sealing of the stem 100 is completed by bringing the inside of the laminated body 21 into a vacuum state by a vacuum pump or the like, and then sealing the opening 23.

In the present embodiment, the sealing body 2 includes a middle part 2A and a pair of side parts 2B and 2B located opposite sides of the middle part 2A, and the stem 100 is intended to be vacuum sealed into the middle part 2A. In other words, the sealing body 2 of the present embodiment is configured to vacuum seal the stem 100 so that the stem 100 is located at the middle part 2A. Each of the pair of side parts 2B and 2B located on the opposite sides of the middle part 2A functions as a region to be wound by a pair of winding parts 5 and 5 of the inner box 3 described later.

A thickness of each of the pair of film materials 22 and 22 described above is preferably 10-300 μm, without being limited thereto. The film material 22 may be a single-layer body or a laminated body. Alternatively, a slit may be formed at a sealing part formed by overlapping the peripheral edge parts 221 and 221 with each other and then sealing together. With this configuration, it is easy to open the sealing body 2 through the slit.

(Inner Box)

The inner box 3 is a member for accommodating the sealing body 2 therein as described above. More specifically, the inner box 3 is the member for accommodating therein the sealing body 2 (pouch) with the stem 100 vacuum sealed therein. The inner box is made of a sheet material 31 having an approximately rectangular shape as shown in FIG. 4. The sheet material 31 is composed of, for example, a cardboard, a cardboard synthetic sheet, a corrugated sheets, or a synthetic resin, such as polyethylene terephthalate, without being limited thereto. The sheet material 31 may be a single-layer body or a laminated body. A thickness of the sheet material 31 is preferably 0.1-1.5 mm, without being limited thereto.

The sheet material 31 is divided into a mounting part 4 and a pair of winding parts 5 and 5, which are sequentially located in a direction from the middle part 3A toward each of a pair of opposing side edge parts 3B and 3B. The mounting part 4 is a region for mounting thereon the middle part 2A of the sealing body 2 described above as shown in FIG. 1(a). Both of the pair of winding parts 5 and 5 are regions intended to windingly fix the side parts 2B of the sealing body 2 extending outward from the mounting part 4 as shown in FIGS. 1(c) and 2, and intended to come into linear contact with the sealing body 2 in the vicinity of a boundary part 6 with the mounting part 4 by winding the pair of winding parts 5 and 5 in an arrowed direction A in the order of FIGS. 1(a) and 1(b). The phrase "coming into linear contact with the sealing body 2" denotes coming into contact with the sealing body 2 in the form of a line. With these configurations, the following effects are obtainable.

That is, the configuration of the package 1 can be made simple because the inner box 3 for accommodating the sealing body 2 therein is made of the single sheet material 31 as described above. This contributes to reducing the number of members discarded, thus leading to cost reduction. Moreover, the sealing body 2 is fixable strongly because both of the pair of winding parts 5 and 5 windingly fix the side parts 2B of the sealing body 2 and come into the linear contact with the sealing body 2. Consequently, the stem 100 is stably packageable.

Therefore, when subjected to vibrations or impacts during transport of the package 1, the loads of the vibrations or impacts can be dispersed, so that the stem 100 is less prone to dislocation. Additionally, the sealing body 2 is fixable in a direction B parallel to a longitudinal direction of the stem 100 which is one of falling directions of the package 1, and in which the stem 100 seems most prone to damage as shown in FIG. 1(a). Therefore, when the package 1 drops in the direction B, an edge part 24 of the sealing body 2 is configured to bend so as to moderate drop impact, so that the stem 100 and the sealing body 2 are less prone to damage.

An area of the mounting part 4 in the present embodiment is approximately identical to an area of the middle part 2A of the sealing body 2. This configuration ensures that the middle part 2A of the sealing body 2 is mounted on the mounting part 4, leading to stable packaging of the stem 100.

As shown in FIG. 4, each of the pair of winding parts 5 and 5 of the present embodiment includes an approximately triangle tubular folding part 50 made up of a first surface 51, a second surface 52, and a third surface 53 which are made of an outer surface 31a of the sheet material 31, and which are located in this order in a direction from the side edge part 3B toward the mounting part 4 in the sheet material 31. With this configuration, the hollow folding part 50 functions as a cushion material, thereby making it possible to moderate the drop impact or the like.

In the present embodiment, an intersecting part 56 of the second surface 52 and the third surface 53 comes into the linear contact with the sealing body 2 when the pair of winding parts 5 and 5 are individually wound up as shown in FIG. 2. In other words, the intersecting part 56 of the second surface 52 and the third surface 53 comes into contact with the sealing body 2 when the pair of winding parts 5 and 5 are individually wound up in the present embodiment. The phrase "the intersecting part 56 comes into the linear contact with the sealing body 2" denotes that the intersecting part 56 substantially comes into the linear contact with the sealing body 2. Specifically, the phrase "the intersecting part 56 comes into the linear contact with the sealing body 2" is not limited to the configuration that the entirety of the intersecting part 56 comes into the linear contact with the sealing body 2. This phrase is the concept that also includes the case where a part of the intersecting part 56 does not come into the linear contact with the sealing body 2. The phrase "the case where a part of the intersecting part 56 does not come into the linear contact with the sealing body 2" corresponds to, for example, the case where a part of the intersecting part 56 is provided with a cutting out.

The third surface 53 is located so as to face the stem 100 when the pair of winding parts 5 and 5 are individually wound up. The third surface 53 has a larger area than each of the first surface 51 and the second surface 52. This configuration ensures a relatively large space S1, which is surrounded by the third surface 53 and the mounting part 4 so as to accommodate the stem 100 therein. The stem 100 and the inner box 3 are less likely to come into contact with each other.

As shown in FIG. 4, each of the pair of winding parts 5 and 5 includes a fourth surface 54 and a fifth surface 55 made of an inner surface 31b of the sheet material 31 which are located between the folding part 50 and the mounting part 4, and are sequentially located in a direction from the folding part 50 toward the mounting part 4. The fourth surface 54 has approximately the same shape as the first surface 51. The fifth surface 55 has approximately the same shape as the second surface 52. As shown in FIG. 2, when the pair of winding parts 5 and 5 are individually wound up, the first surface 51 and the fourth surface 54 are opposed to each other, and the second surface 52 and the fifth surface 55 are opposed to each other. In the present embodiment, the side part 2B of the sealing body 2 is configured to be windingly fixed between the second surface 52 and the fifth surface 55. Alternatively, the side part 2B of the sealing body 2 may be windingly fixed between the first surface 51 and the fourth surface 54.

Figure 2A:
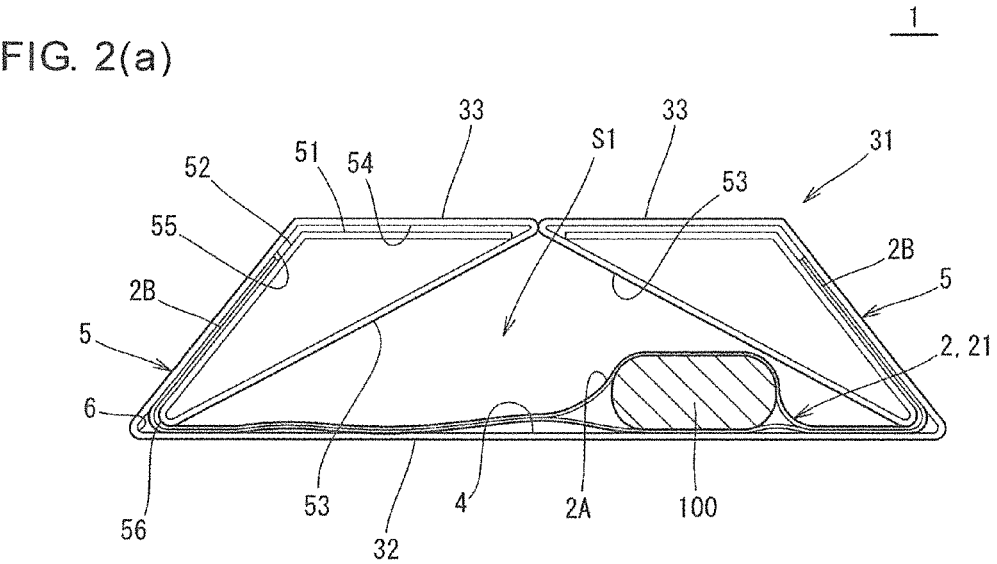
FIG. 2(a) is a diagram showing, in an enlarged dimension, a schematic broken surface diagram taken along line 2a-2a in FIG. 1(c)

When the pair of winding parts 5 and 5 are individually wound into the inner box 3 of the present embodiment having the above-mentioned configuration, the inner box 3 is made into such an approximately trapezoidal shape that a region of the sheet material 31 which corresponds to the mounting part 4 serves as a bottom surface 32 and a region of the sheet material 31 which corresponds to the fourth surface 54 serves as a top surface 33 as shown in FIG. 2(a).

The inner box 3 of the present embodiment has finger insertion holes 34 (refer to FIG. 1(c)) each of which penetrates regions respectively corresponding to the first surface 51 and the fourth surface 54 in the sheet material 31. With this configuration, the wound winding parts 5 are openable by inserting a finger into the finger insertion holes 34. The number of the finger insertion holes 34 may be at least one. The number of the finger insertion holes 34 of the present embodiment is two, which are respectively disposed in the pair of winding parts 5 and 5.

Figure 4A:
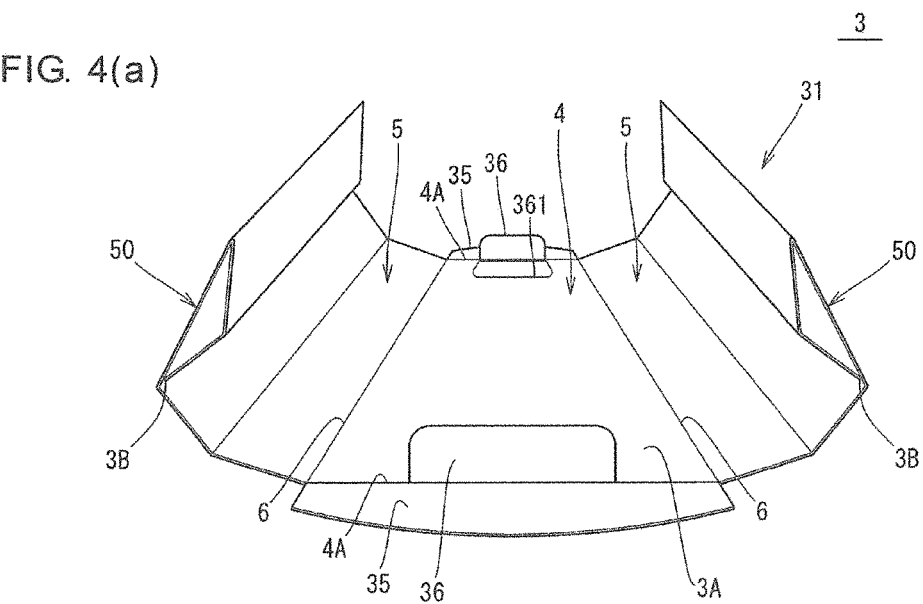
FIG. 4(a) is a perspective view thereof.
Figure 4B:
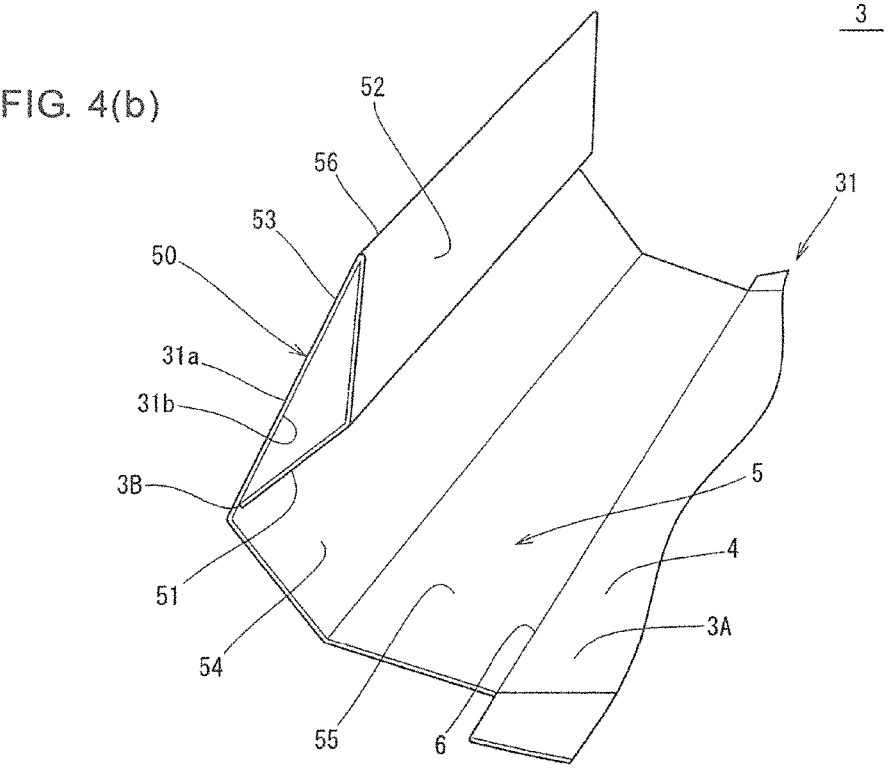
FIG. 4(b) is a diagram showing a part of FIG. 4(a) in an enlarged dimension.

As shown in FIG. 4(a), the inner box 3 of the present embodiment further includes a holding part 35 extending outward from at least one of the pair of opposing edge parts 4A and 4A of the mounting part 4. More specifically, the inner box 3 includes the holding part 35 extending outward from at least one of the pair of edge parts 4A and 4A in the longitudinal direction of the mounting part 4 having an approximately rectangular shape. The holding part 35 of the present embodiment extends outward from each of the pair of edge parts 4A and 4A. With this configuration, the inner box 3 being accommodated in an outer box 7 described later can be smoothly taken out by holding the holding part 35.

The holding part 35 of the present embodiment is formed integrally with the mounting part 4. This configuration contributes to improving connection strength between the holding parts 35 and the mounting part 4. Alternatively, the holding parts 35 may be made of a material other than that of the mounting part 4 as needed.

The inner box 3 of the present embodiment further includes an anti-slip part 36 located in the vicinity of at least one of the pair of opposing edge parts 4A and 4A of the mounting part 4. The anti-slip part 36 of the present embodiment is located along each of the pair of edge parts 4A and 4A. With this configuration, the sealing body 2 is less likely to slide along the mounting part 4 and drop out of the inner box 3.

The anti-slip part 36 of the present embodiment is one in which a slit 361 is formed along a shape of the anti-slip part 36 on the mounting part 4, and a region surrounded by the slit 361 is raised. With this configuration, the anti-slip part 36 is integrated with the mounting part 4, thus making it possible to improve the connection strength between the anti-slip part 36 and the mounting part 4. Alternatively, the anti-slip part 36 may be made of a material other than that of the mounting part 4 as needed.

Figure 1B:
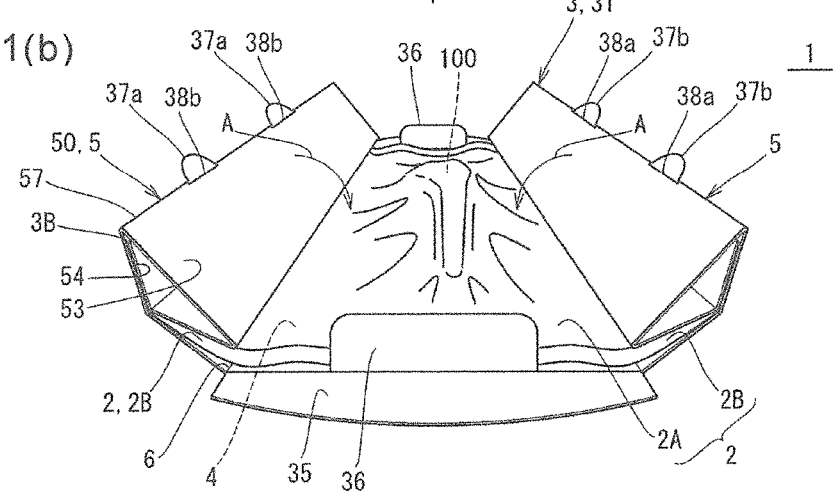
Figure 1C:
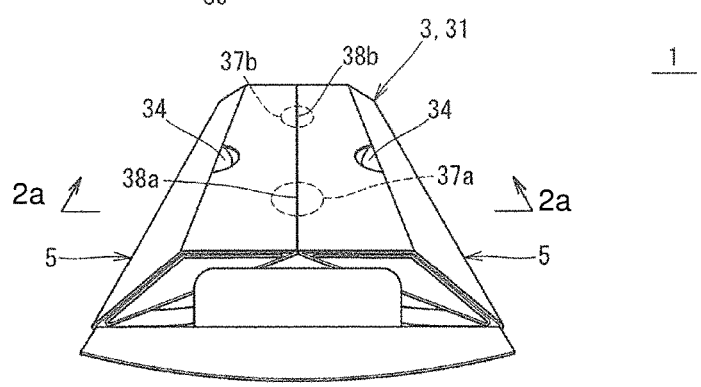
Figure 2B:
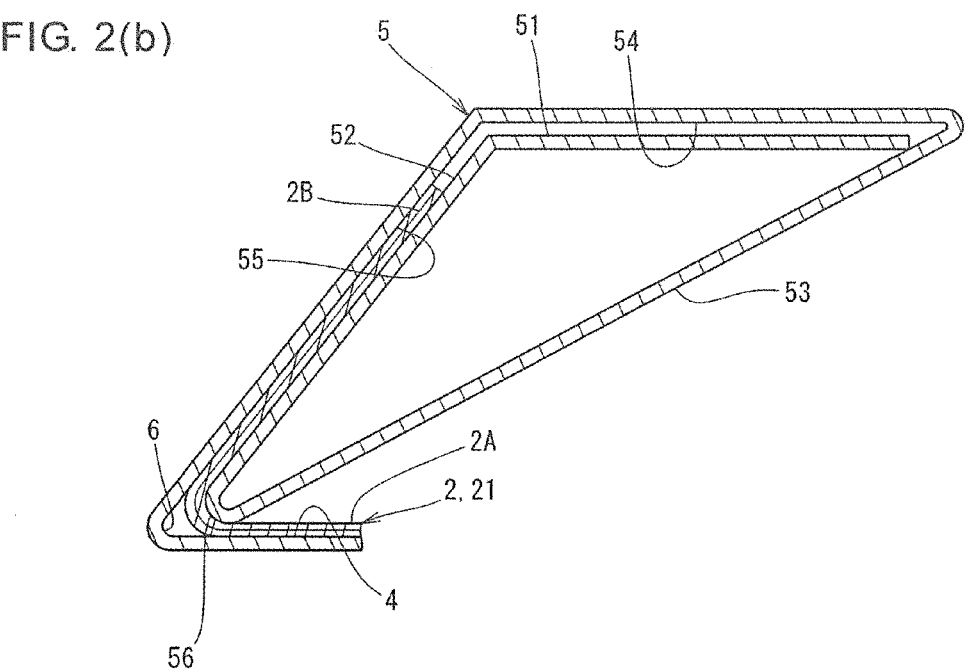
FIG. 2(b) is a diagram showing a part of FIG. 2(a) in an enlarged dimension.

As shown in FIGS. 1(b) and 1(c), the inner box 3 of the present embodiment further includes a plurality of engagement pieces 37a and 37b and a plurality of insertion holes 38a and 38b. Of these, the engagement piece 37a and the insertion hole 38a are exemplified in the following description. The engagement piece 37a and the insertion hole 38a are located so as to face each other when the pair of winding parts 5 and 5 are wound up. The engagement piece 37a is located at one of the pair of winding parts 5 and 5, and extends toward another winding part 5. The insertion hole 38a is located at the another winding part 5 and configured to permit insertion of the engagement piece 37a. With these configurations, the state in which the pair of winding parts 5 and 5 are wound up is retainable by inserting the engagement piece 37a into the insertion hole 38a. These points are also true for the engagement piece 37b and the insertion hole 38b.

Of the engagement pieces 37a and 37b and the insertion holes 38a and 38b, the engagement piece 37a and the insertion hole 38b which are located at the one winding part 5 are exemplified in the following description. The engagement piece 37a and the insertion hole 38b have the following configurations. That is, as shown in FIG. 1(b), the engagement piece 37a extends from the side edge part 3B. The insertion hole 38b is located at a region 57 of the sheet material 31 which corresponds to a boundary part between the third surface 53 and the fourth surface 54. The engagement piece 37a extends toward the another winding part 5 while being inserted into the insertion hole 38b. With these configurations, the shape of the above-mentioned approximately triangle tubular folding part 50 is retainable by inserting the engagement piece 37a into the insertion hole 38b. These points are also true for the engagement piece 37b and the insertion hole 38a. In the present embodiment, the two engagement pieces 37a and the two insertion holes 38b are included in the one winding part 5, and the two engagement pieces 37b and the two insertion holes 38a are included in the another winding part 5. However, the number of the engagement pieces 37a and 37b and the insertion holes 38a and 38b are not limited thereto.

(Outer Box)

Figure 5A:
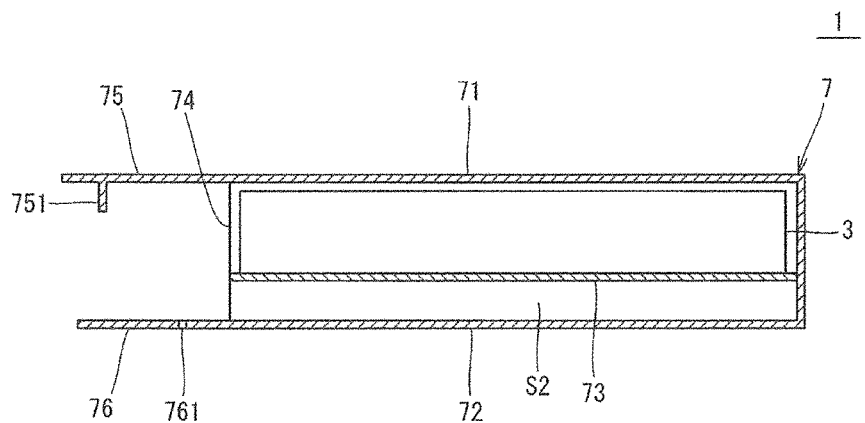
FIG. 5(a) is a schematic cross-sectional explanatory diagram showing a state before closing an opening.
Figure 5B:
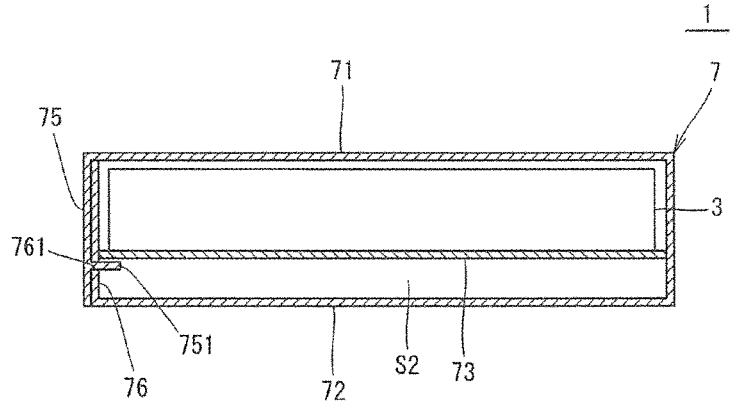
FIG. 5(b) is a schematic cross-sectional explanatory diagram showing a state after closing the opening.

The package 1 of the present embodiment further includes the outer box 7 as shown in FIG. 5. The outer box 7 is a member for accommodating the inner box 3 therein, more specifically a member for accommodating therein the inner box 3 accommodating the sealing body 2 therein. As a material constituting the outer box 7, there are, for example, cardboard sheets, synthetic cardboard sheets, corrugated cardboard sheets, and synthetic resins, such as polyethylene terephthalate, without being limited thereto. The outer box 7 may be made of a single layer body of the material described above, or a laminated body. A thickness of the outer box 7 is preferably 0.1-2.5 mm, without being limited thereto.

The outer box 7 includes a raising part 73 which is capable of mounting the inner box 3 and located with a space S2 from a bottom surface 72. This configuration ensures that the bottom surface 72 is raised by the raising part 73. Therefore, when the inner box 3 is accommodated in the outer box 7, the space S2 is left between the inner box 3 and the bottom 72. Consequently, drop impact exerted from a direction passing through the bottom surface 72 can be moderated by the space S2. Moreover, the space S2 is capable of accommodating therein, for example, an attached document about the stem 100. Although the raising part 73 of the present embodiment has an approximately planar shape, no particular limitation is imposed on the shape thereof as long as it is capable of mounting the inner box 3 thereon.

The outer box 7 further includes an opening 74 that permits loading and unloading of the inner box 3, and a first side surface 75 and a second side surface 76 which are configured to openably and closably close the opening 74 by being overlapped with each other. The first side surface 75 and the second side surface 76 are configured so as to close the opening 74 in the order of the second side surface 76 and the first side surface 75. The first side surface 75 has a claw part 751 that is located close to the raising part 73 in the space S2 when the opening 74 is being closed. The second side surface 76 has a through hole 761 that permits insertion of the claw part 751. With these configurations, a state in which the opening 74 is closed by the first side surface 75 and the second side surface is retainable by causing the claw part 751 to be inserted into the through hole 761. For example, when the attached document about the stem 100 is accommodated in the space S2, the attached document is less likely to be caught between the claw part 751 and the bottom surface 72. The first side surface 75 connects to the top surface 71 of the outer box 7, and the second side surface 76 connects to the bottom surface 72 of the outer box 7 in the present embodiment, without being limited thereto.

<Bioimplant Packaging Method>

The bioimplant packaging method according to an embodiment of the present invention is described in detail below by illustrating, for example, the above-mentioned package 1.

The packaging method of the present embodiment includes the following first to third steps.

The first step includes vacuum sealing the stem 100 by the sealing body 2 so that the stem 100 is located at the middle part 2A of the sealing body 2 as shown in FIG. 3.

The second step includes accommodating the sealing body 2 into the inner box 3 in a state in which the side parts 2B and 2B of the sealing body 2 extending outward from the mounting part 4 are windingly fixed and also brought into the linear contact with the sealing body 2 in the vicinity of the boundary part 6 with the mounting part 4, namely, brought into contact with the sealing body in the form of a line, as shown in FIGS. 1(c) and 2, by winding the pair of winding parts 5 and 5 in the arrowed direction A in the order of FIGS. 1(a) and 1(b) after mounting the middle part 2A of the sealing body 2 on the mounting part 4 of the inner box 3 as shown in FIG. 1(a).

The third step includes obtaining the package 1 by finally accommodating the inner box 3 into the outer box 7 as shown in FIG. 5.

Depressurized conditions when vacuum sealing the stem 100 by the sealing body 2 in the first step described above need to be conditions under which an air pressure inside the sealing body 2 is lower than at least atmospheric pressure. Examples of depressurizing means include a vacuum pump.

The sealing body 2 with the stem 100 vacuum sealed therein is preferably subjected to sterilization treatment. Examples of the sterilization treatment include radiation sterilization treatment. The radiation sterilization treatment can be carried out by, for example, irradiating gamma ray or electron beam to the sealing body 2 with the stem 100 vacuum sealed therein.

When the inner box 3 is accommodated into the outer box 7 in the third step, it is necessary to bring into a state in which the holding part 35 is bent toward the top surface 33 of the inner box 3.

While the present invention has been described above in terms of preferable embodiments, it is to be understood that the present invention is not limited to the foregoing embodiments and may be made into any optional ones insofar as they do not depart from the spirit and scope of the present invention.

For example, even though the bioimplant is the stem 100 in the foregoing embodiment, the package 1 is capable of packaging a bioimplant other than the stem 100.

Although the sealing body 2 is constituted by the laminated body 21 in the foregoing embodiment, the sealing body 2 is not limited thereto insofar as it is possible to vacuum seal the stem 100. As other configuration of the sealing body 2, there is, for example, such a configuration that an approximately rectangular-shaped film material 22 is folded into two, and peripheral edge parts except for a bent portion are overlapped with each other and sealed together, a configuration for sealing the opening of a so-called film pack.

Although the present invention is described in detail below by illustrating an example, the present invention is not limited to the following example.

EXAMPLES

The above-mentioned package 1 was subjected to a vibration test and a drop test. The configuration of the package 1 and various test conditions were as follows.

(Configuration of Package 1)

A film material 22 constituting the sealing body 2: a laminated body of a polyethylene film with a thickness of 15 μm and a polyamide film with a thickness of 75 μm A sheet material 31 constituting the inner box 3: a cardboard with a thickness of 0.4 mm Material constituting the outer box 7: a laminated body with a thickness of 1.7 mm made up of a corrugated cardboard sheet and a cardboard synthetic sheet Others: a configurations other than the above matters are as shown in FIGS. 1 to 5.

(Vibration Test Conditions)

Atmospheric temperature: room temperature (23° C.)
Test form: single axis vibration test
Frequency: 22-44 Hz (0.5 octave/min)
Amplitude: 2.0 mm or more
Test time: 60 minutes for each of X axis, Y axis, and Z Axis (Drop Test Conditions)

Figure 6A:
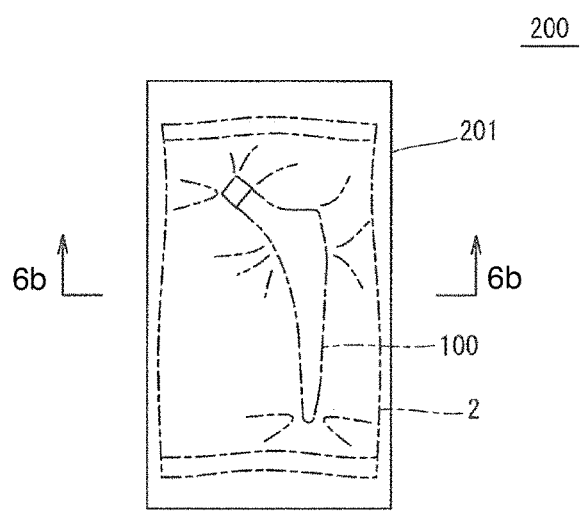
FIG. 6(a) is a schematic plan view thereof.
Figure 6B:
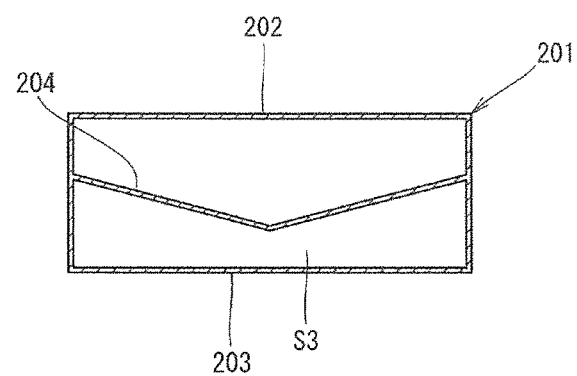
FIG. 6(b) is a diagram showing, in an enlarged dimension, a sectional view taken along line 6a-6a in FIG. 6(a).

Atmospheric temperature: room temperature (23° C.)
Drop form: free drop
Drop height: 2 m
Floor surface receiving drops: concrete surface
Drop direction: a direction in which a distal end 101 of the stem 100 shown in FIG. 3(a) is directed to the floor surface receiving drops
Number of drops: three Comparative Example The stem 100 was vacuum sealed into the sealing body 2 in the same manner as in Example. The sealing body 2 was then accommodated into an outer box 201 shown in FIG. 6. More specifically, the outer box 201 was made of a cardboard with a thickness of 0.7 mm, and a top surface 202 is configured to be openable and closable. The outer box 201 includes a raising part 204 located with a space S3 from a bottom surface 203 in the inside of the outer box 201. The raising part 204 was configured to be made into an approximately V-shape in a sectional view by combining a pair of flat plates. A bioimplant package 200 was obtained by mounting the above-mentioned sealing body 2 with the stem 100 vacuum sealed therein on the raising part 204, and then accommodating the sealing body 2 in the outer box 201 in a state in which a pair of side parts 2B and 2B of the sealing body 2 was bent. The obtained package 200 was subjected to the vibration test and the drop test in the same manner as in Example.

As a result of the vibration test and the drop test, the package 1 of Example caused no damage to the stem 100, the sealing body 2, the inner box 3, and the outer box 7 in each of the vibration test and the drop test.

In contrast, the package 200 of Comparative Example caused damage to the stem 100, the sealing body 2, and the outer box 201 because the distal end 101 of the stem 100 broke through the sealing body 2 in each of the vibration test and the drop test.

DESCRIPTION OF THE REFERENCE NUMERAL 1 bioimplant package
2 sealing body
2A middle part
2B side part
21 laminated body
22 film material
221 peripheral edge part
23 opening
3 inner box
3A middle part
3B side edge part
31 sheet material
31a outer surface
31b inner surface
32 bottom surface
33 top surface
34 finger insertion hole
35 holding part
36 anti-slip part
361 slit
37a, 37b engagement piece
38a, 38b insertion hole
4 mounting part
4A edge part
5 winding part
50 folding part
51 first surface
52 second surface
53 third surface
54 fourth surface
55 fifth surface
56 intersecting part
57 region
6 boundary part
7 outer box
71 top surface
72 bottom surface
73 raising part
74 opening
75 first side surface
751 claw part
76 second side surface
761 through hole
100 artificial hip joint stem
200 bioimplant package
201 outer box
202 top surface
203 bottom surface
204 raising part

The invention claimed is:

1. A bioimplant package comprising:
   a sealing body composed of a gas impermeable film material and configured to vacuum seal a bioimplant therein; and
   an inner box configured to accommodate the sealing body therein,
   wherein the sealing body is configured to vacuum seal the bioimplant so that the bioimplant is located at a middle part of the sealing body, and
   wherein the inner box comprises an approximately rectangular-shaped sheet material divided into a mounting part configured to mount thereon the middle part of the sealing body, and a pair of winding parts configured to windingly fix a side part of the sealing body extending outward from the mounting part and configured to come into linear contact with the sealing body in a vicinity of a boundary part with the mounting part, in which the mounting part and the pair of winding parts are located sequentially in a direction from a middle part toward each of a pair of opposing side edge parts in the inner box.

2. The bioimplant package according to claim 1, wherein each of the pair of winding parts comprises an approximately triangle tubular folding part comprising a first surface, a second surface, and a third surface which are composed of an outer surface of the sheet material, and which are located sequentially in a direction from the side edge part toward the mounting part in the sheet material.

3. The bioimplant package according to claim 2, wherein an intersecting part of the second surface and the third surface is configured to come into linear contact with the sealing body when the pair of winding parts are individually wounded up.

4. The bioimplant package according to claim 2, wherein the third surface is located so as to face the bioimplant when the pair of winding parts are individually wounded up, and the third surface has a larger area than each of the first surface and the second surface.

5. The bioimplant package according to claim 2, wherein each of the pair of winding parts comprises a fourth surface and a fifth surface which are composed of an inner surface of the sheet material, and which are located between the folding part and the mounting part and located sequentially in a direction from the folding part toward the mounting part.

6. The bioimplant package according to claim 5,
wherein the fourth surface has approximately a same shape as the first surface,
wherein the fifth surface has approximately a same shape as the second surface, and
wherein the first surface and the fourth surface are opposed to each other, and the second surface and the fifth surface are opposed to each other when the pair of winding parts are individually wounded up.

7. The bioimplant package according to claim 5, wherein the inner box is made into such an approximately trapezoidal shape that a region of the sheet material which corresponds to the mounting part serves as a bottom surface and a region of the sheet material which corresponds to the fourth surface serves as a top surface.

8. The bioimplant package according to claim 5, wherein the inner box comprises a finger insertion hole penetrating regions respectively corresponding to the first surface and the fourth surface of the sheet material.

9. The bioimplant package according to claim 1, wherein the inner box comprises a holding part extending outward from at least one of a pair of opposing edge parts of the mounting part.

10. The bioimplant package according to claim 1, wherein the inner box comprises an anti-slip part located in a vicinity of at least one of a pair of opposing edge parts of the mounting part.

11. The bioimplant package according to claim 1, wherein the inner box comprises an engagement piece located at one of the pair of winding parts and extending toward another winding part, and an insertion hole located at the another winding part and configured to permit insertion of the engagement piece, in which the engagement piece and the insertion hole are located so as to face each other when the pair of winding parts are individually wounded up.

12. The bioimplant package according to claim 1, further comprising an outer box configured to accommodate the inner box therein.

13. The bioimplant package according to claim 12, wherein the outer box comprises a raising part which is located with a space from a bottom surface of the outer box, and is capable of mounting thereon the inner box in an interior of the outer box.

14. The bioimplant package according to claim 13, wherein the outer box comprises
an opening configured to permit loading and unloading of the inner box, and
a first side surface and a second side surface which are configured to openably and closably close the opening by being overlapped with each other,
wherein the second side surface and the first side surface are configured to close the opening in this order,
wherein the first side surface comprises a claw part located close to the raising part in the space when the opening is being closed, and
wherein the second side surface comprises a through hole configured to permit insertion of the claw part.

15. The bioimplant package according to claim 1, wherein the bioimplant is an artificial hip joint stem.

16. A bioimplant packaging method for packaging a bioimplant by using the bioimplant package according to claim 1, the method comprising:
vacuum sealing the bioimplant by the sealing body so that the bioimplant is located at the middle part of the sealing body; and
accommodating the sealing body into the inner box in a state in which the side parts of the sealing body extending outward from the mounting part are windingly fixed and also brought into linear contact with the sealing body in a vicinity of the boundary part with the mounting part, by winding each of the pair of winding parts after mounting the middle part of the sealing body on the mounting part of the inner box.

* * * * *